United States Patent [19]

Anderson et al.

[11] 4,264,518

[45] Apr. 28, 1981

[54] UNSATURATED CARBOXYLIC ACIDS AND ESTERS

[75] Inventors: Richard J. Anderson; Clive A. Henrick, both of Palo Alto, Calif.

[73] Assignee: Zoecon Corporation, Palo Alto, Calif.

[21] Appl. No.: 956,292

[22] Filed: Oct. 30, 1978

[51] Int. Cl.³ .................. C07C 57/00; C07C 69/52
[52] U.S. Cl. ............................ 260/410.9 R; 260/413; 260/456 R; 260/665 G; 568/840; 570/189
[58] Field of Search ............... 560/205; 562/598; 424/84; 260/410.9 R, 413

[56] References Cited

U.S. PATENT DOCUMENTS 843,290   2/1907   Moureu .................... 560/205
3,235,570   2/1966   Phillips et al. ............ 560/205

OTHER PUBLICATIONS

Keppeler, H. et al., "Synthesis and Cyclization of 3,7-Dimethyl-2,7-Octadienoic Acid: . . . " Helv. Chim. Acta 37, 957–964, (1954), See Chemical Abstract vol. 49, #5327b, (1955).

*Primary Examiner*—Natalie Trousof
*Assistant Examiner*—L. Hendriksen
*Attorney, Agent, or Firm*—Donald W. Erickson

[57] ABSTRACT

Synthesis and intermediates for making an insect pheromone useful in the control of the San Jose scale, *Quadraspidiotus perniciosus*.

4 Claims, No Drawings

UNSATURATED CARBOXYLIC ACIDS AND ESTERS

This invention relates to the synthesis of the sex pheromone of the San Jose scale, *Quadraspidiotus perniciosus* (Comstock), and intermediates therefor. The San Jose scale is a pest of fruit crops.

The sex pheromone is made up of the following two components in about a 1:1 ratio:

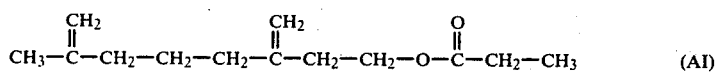  (AI)

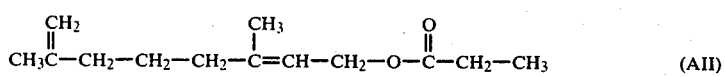  (AII)

The synthesis of component AI can be outlined as follows:

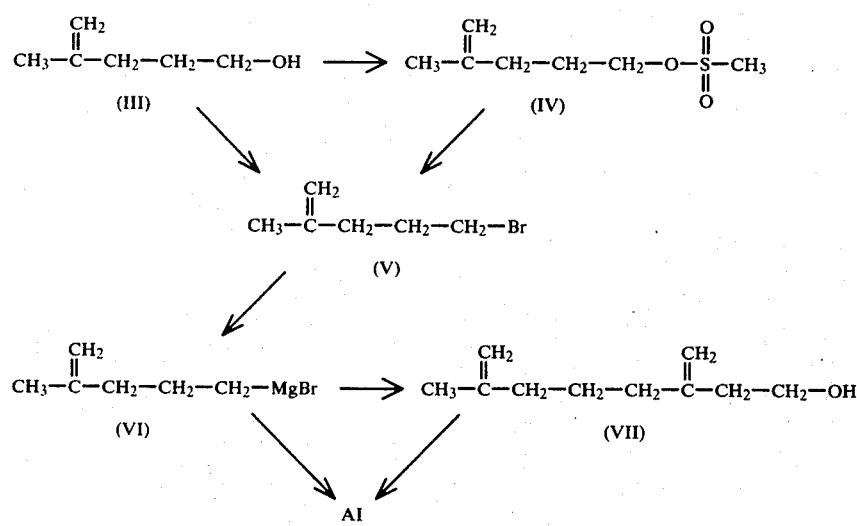

In the practice of the above synthesis of component AI, 4-methyl-4-penten-1-ol (III) is converted to bromide (V) with bromine in the presence of triphenylphosphine and pyridine. Alternately, 4-methyl-4-penten-1-ol is reacted with mesyl chloride and triethylamine to give the corresponding mesylate (IV), which is then reacted with sodium bromide. The bromide (V) resulting from either of these methods is reacted with magnesium, in the presence of ether, forming a Grignard reagent (VI). This Grignard reagent is reacted with cuprous bromide/dimethyl sulfide complex and trimethylsilyl 3-butynyl ether to make the alcohol (VII), which is treated with propionic anhydride in pyridine to yield compound AI.

Alternately, the Grignard reagent VI may be reacted with the cuprous bromide/dimethyl sulfide complex and 3-butyn-1-yl propionate, in ether, giving the compound AI.

The synthesis of component AII is outlined below:

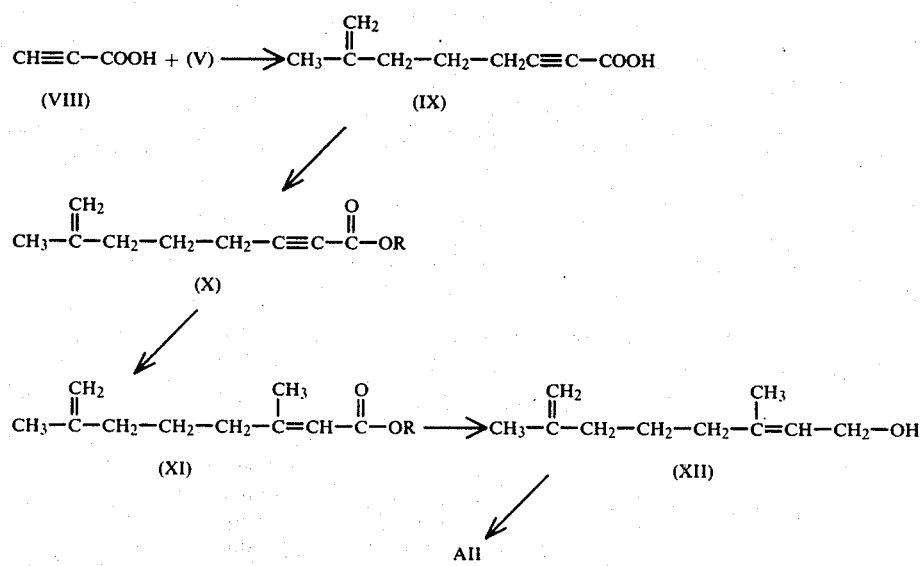

In the practice of the synthesis of compound AII, propiolic acid (VIII) and the bromide V are reacted, in the presence of t-butyllithium and ether, to give the carboxylic acid (IX), which is then esterified to compound X (R is lower alkyl of one to six carbon atoms). The acetylenic ester X is methylated following the procedure of R. J. Anderson et al., *J. Am. Chem. Soc.*, 97, 1197 (1975) to the diene ester (XI), which is then reduced to the corresponding alcohol (XII) by reaction with diisobutyl aluminum hydride in heptane. Esterification of the diene alcohol, with propionic anhydride and pyridine, follows to yield compound AII.

Alternately, compound XI above may be synthesized as follows:

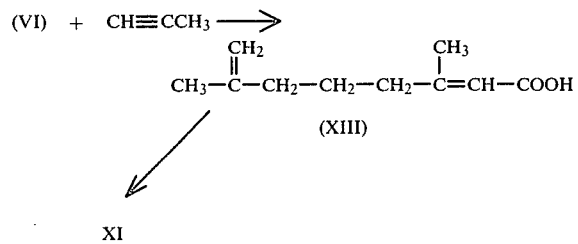

The diene ester XI may also be synthesized by reaction of the Grignard reagent VI with propyne and cuprous bromide/dimethyl sulfide complex in the presence of carbon dioxide, triethylphosphite and hexamethylphosphoramide (HMPA) to give the diene carboxylic acid (XIII). The acid is esterified using diazomethane or the like and ether to the compound XI.

Each of the two components of the San Jose scale sex pheromone, AI (7-methyl-3-methylene-7-octen-1-yl propionate) or AII [(Z)-3,7-dimethyl-2,7-octadien-1-yl propionate], is individually active as an attractant for San Jose scale. Both of the components of the sex pheromone, either individually or in combination in a ratio of about 1:1, by weight, are useful in conjunction with traps to monitor populations of, or to mass trap, the San Jose scale, attracting the male or the female or both. The amount of compound employed per trap is very small. Generally, there is used from about 100 to 1,000 micrograms of compound per trap. The sex pheromone is useful also in the confusion technique of insect control which involves releasing an excessive amount of the compound, whereby the insects are disoriented and unable to mate. Suitable carriers for the phermone components include rubber and plastic septums, which can then be placed in traps having an adhesive coating. The components may also be blended with a plastic such as polyvinyl chloride for ease of handling and dispensing. Suitable carriers, diluents and traps are described in U.S. Pat. Nos. 3,866,349, 4,034,080 and 4,083,995.

The following examples are provided to illustrate the practice of the present invention. Temperature is given in degrees Centigrade and RT means room temperature.

EXAMPLE 1

A. A solution of 53.4 g of triphenylphosphine (203.7 mmol) in 600 ml methyl cyanide, under nitrogen, is cooled in an ice bath, and then 32.4 g (202.7 mmol) of bromine in 200 ml methyl cyanide is added, followed by 16.04 g pyridine and then by 4-methyl-4-penten-1-ol (20 g, 200 mmol) in 35 ml of methyl cyanide. The mixture is allowed to stand overnight. The reaction is worked up by adding water and extracting with pentane (3X). The pentane layers are washed with 2 B HCl (2X), water (2X) and brine, and dried over sodium sulfate. Solvent is removed by distillation to yield 1-bromo-4-methyl-4-pentene.

B. To 1.3 g magnesium (51.8 mmol) and 10 ml ether, under nitrogen, is added a small amount (approximately 8 drops) of 1-bromo-4-methyl-4-pentene. After the reaction has begun, 10 ml ether is added, followed by the remainder of the bromide 7.6 g total, 47.2 mmol) in 20 ml ether. After addition of the bromide, 20 ml more ether is added to the reaction, which is then heated overnight to yield 4-methyl-4-penten-1-ylmagnesium bromide.

C. Ten grams of cuprous bromide and 20 ml of dimethyl sulfide are mixed together, then filtered. To the filtrate is added 50 ml of hexane and a reddish-white solid precipitates. This is filtered, and the solid is washed with hexane until the washings are no longer colored. The solid is then dissolved in 30 ml of dimethyl sulfide and about 100 ml of hexane is slowly added. The solid (cuprous bromide/dimethyl sulfide complex) which forms is collected and dried over $P_2O_5$ under vacuum overnight.

2.1 Grams (10.0 mmol) of the above complex is suspended in 15 ml of dry ether, and 12 ml of dimethyl sulfide is added under nitrogen. The resulting solution is cooled to $-60°$ and another 14 ml of dimethyl suflide is added to dissolve the precipitate that forms. The Grignard reagent (24 ml, 9.6 mmol) from B above is added at $-60°$ over 5 min and the reaction is stirred at $-45°$ for 2 hr. Trimethylsilyl 3-butynyl ether (1.4 g, 9.8 mmol) (preparation follows) in ether/pentane (5 ml/30 ml) is added at $-45°$; the mixture is allowed to warm to $-25°$ with stirring for several hours. The reaction is then poured into a pre-cooled ($< -10°$) solution of HCl/sat. $NH_4Cl$, allowed to warm to RT and stirred overnight. The reaction is worked up by water and extraction with ether (2X). The ether phases are combined, washed with sat $(NH_4)_2SO_4$, water and brine, filtered and solvent removed to give 7-methyl-3-methylene-7-octen-1ol.

Trimethylsilyl 3-butynyl ether can be made as follows: 3.5 grams of 3-butyn-1-ol (50.0 mmol) is diluted to 50 ml with pentane, and 11 ml of ether is then added. This mixture is stirred under nitrogen and cooled in an ice bath. Triethylamine (9.2 ml, 66 mmol) is added, followed by the slow addition of trimethylsilyl chloride (7.6 ml, 59.9 mmol); the mixture is stirred at 10° for 2 hr. Approximately 30 ml ice-cold water is added and the phases are separated. The organic layer is extracted quickly with ice-cold 1 N $H_2SO_4$ (2X), sat. $NaCHO_3$ and brine, and dried over $Na_2SO_4$, giving trimethylsilyl 3-butynyl ether.

D. A mixture of 0.27 g of 7-methyl-3-methylene -7-octen-1-ol (1.8 mmol), 1.0 ml propionic anhydride (7.8 mmol) and 1.0 ml pyridine (12.4 mmol), under nitrogen, is heated to 65° for 1 hr. Ice is added and the mixture stirred for 30 min at RT. The mixture is worked up by partition between ether/water. The aqueous phase is extracted with ether. The ether extracts are combined and washed with 2 N HCl (2X), sat. $NaHCO_3$ and brine; and dried over $MgSO_4$. The crude product, after removal of solvent, is purified by preparative thin layer chromatography on silica gel plates developing with 4% ether/hexane to yield 7-methyl-3-methylene-7-octen-1yl propionate.

Nmr (CDCl₃) δ1.51 (t, J=7 Hz, ROC-OCH₂CH₃), 1.75 (s, 3H, vinyl methyl), 4.20 (t, J=7 Hz, 2H, CH₂OC=O), 4.72 (s, 2H, methylene) and 4.80 ppm (s, 2H, methylene).

Ir (neat) 1735 cm⁻¹ (C=O).

B.p. 68°–72° (oil bath) @ 1.0 mm Hg.

EXAMPLE 2

A mixture of 5.0 g 3-butyn-1-ol (71.3 mmol), 35 ml of propionic anhydride (273 mmol) and 25 ml of pyridine (309 mmol) is heated at 65°, under nitrogen, in an oil bath. After 1 hr, ice is added and the mixture stirred at RT. The reaction is worked up by partitioning between 2 N HCl/ether. The layers are separated and the aqueous layer is extracted 2× with ether. The ether extracts are combined and washed with 2 N HCl until the washes are acidic (4×), then with 5% NaOH (3×), water and brine, dried over MgSO₄ and filtered, and the solvent is removed by distillation.

Cuprous bromide/dimethyl sulfide complex (0.61 g, 3 mmol) (prepared as in Example 1C) is cooled, together with 5 ml ether and 17 ml dimethyl sulfide, to −50°; the 18 ml (2.7 mmol) of 4-methyl-4-penten-1-yl magnesium bromide (as from Example 1B) is added dropwise, maintaining the temperature of the mixture below −45°. The mixture is warmed to −40° and 0.37 g (2.9 mmol) of 3-butyn-1-yl propionate, in 5 ml ether, is added, after which the mixture is allowed to warm to −25°. After 4 hr, the mixture is cooled to −40°, 10 ml of sat. NH₄CH is added, and the mixture is allowed to warm to RT slowly overnight. The reaction is worked up by partitioning between ether/sat. NH₄Cl. The layers are separated and the aqueous phase is extracted with ether (2×). The ether phases are combined, washed with sat NH₄Cl, water and brine, and dried over MgSO₄, yielding, after removal of the solvent, 7-methyl-3-methylene-7-octen-1-yl propionate.

EXAMPLE 3

4-Methyl-4-penten-1-ol (10.0 g, 0.10 mmol) is placed in 100 ml dry methylene chloride and cooled, with stirring and under nitrogen, in an acetone/dry ice bath to 0°. Triethylamine (42 ml, 0.30 mmol) is added all at once, followed by mesyl chloride (12 ml, 0.16 mmol) over a 15 min period. The mixture is stirred at 0° for 2 hr and then water is added, followed by stirring for 5 min. The mixture is worked up by extraction with water and the layers are separated. The aqueous phase is extracted with methylene chloride (2×); the organic layers are combined and washed with sat. NaHCO₃, 2 N HCl, water and brine, dried over MgSO₄, filtered and evaporated (not to dryness), giving 4-methyl-4-pentenyl methanesulfonate.

The above mesylate (0.10 mol) and sodium bromide (15.5 g, 0.15 mol) are combined in 100 ml hexamethylphosphoramide (HMPA) and stirred at RT under nitrogen for 3 days. The reaction is partitioned between pentane/water and the layers are separated. The aqueous layer is extracted with pentane (2×). The organic phases are combined, washed with water (3×) and brine (2×), dried over MgSO₄ and filtered, and the solvent is removed by distillation to give 1-bromo-4-methyl-4-pentene.

Following the methods of either Example 1 or Example 2, the 1-bromo-4-methyl-4-pentene is converted to the final product, 7-methyl-3-methylene-7-octen-1-yl propionate.

EXAMPLE 4

A. 0.13 Gram (1.85 mmol) propiolic acid is dissolved in 20 ml ether, under nitrogen, and the solution is cooled to −70°. 3.3 Milliliters of 1.1 M t-butyllithium (3.63 mmol) is added over a period of 1 hr, and the mixture is stirred for an additional hour at −60°. HMPA (10 ml) is added, followed by 0.32 g (1.96 mmol) 1-bromo-4-methyl-4-pentene (prepared as in either Example 1 or Example 3), keeping the solution cold. After 24 hr, the mixture is heated to 40°–45°. After 3 days, the reaction is worked up in 5% NaOH/ether, and the aqueous layer is extracted with ether. The basic phase is acidified with HCl and extracted with ether (2×). The latter ether phases are washed with water and brine, dried over Na₂SO₄, filtered and the solvent is removed to yield 7-methyl-7-octen-2-ynoic acid.

Nmr (CDCl₃)δ1.73 (s, 3, CH₃C=C), and 4.73 ppm (br s, 2, C=CH₂).

B. A mixture of 0.18 g (1.18 mmol) of 7-methyl-7-octen-2-ynoic acid, 0.19 g (1.37 mmol) of potassium carbonate and 0.18 g (1.27 mmol) of methyl iodide, in 0.75 ml ether and 0.10 ml HMPA, is stirred overnight under nitrogen. The reaction is worked up in ether/water. The aqueous layer is extracted with ether (2×); the ether layers are then combined and washed with water and brine, dried over Na₂SO₄ and filtered, and the solvent is removed, giving the methyl ester of 7-methyl-7-octen-2-ynoic acid.

Nmr (CDCl₃) δ1.74 (s, 3, CH₃C=CH₂), 3.79 (s, 3, CO₂CH₃), and 4.75 ppm (br s, 2, C=CH₂).

C. To 11.0 mmol of cuprous iodide in 30 ml of dry diethyl ether at −40° under nitrogen is added 10.6 mmol of methyllithium in hexane, followed immediately by 13.0 mmol of tetramethylethylenediamine (TMEDA). After stirring for 30 min, the suspension is cooled to about −50°, and 10 mmol of the methyl ester of 7-methyl-7-octen-2-ynoic acid in 1 ml ether is added dropwise. The temperature is maintained at −45° to −50° for 20 min and then 2 ml of methanol is added dropwise to quench the reaction, followed by 1 ml sat. (NH₄)₂SO₄. The suspension is allowed to warm to RT, after which the solid is filtered off and washed with ether. The combined organic layers are washed with sat. (NH₄)₂SO₄, 5% HCl, sat. NaHCO₃ and brine, then dried over CaSO₄. The solvent is removed by distillation, yielding the Z methyl ester of 3,7-dimethyl-2,7-octadienoic acid.

D. To 1.13 g (6.2 mmol) of the above methyl ester in 10 ml benzene, cooled in an ice bath under nitrogen, is added 8.4 ml of a 27.8% diisobutyl aluminum hydride (DIBAH) in heptane solution (approximately 15 mmol of DIBAH). After 1 hr, an additional 3 ml of DIBAH is added. After the reaction is complete, the excess DIBAH is quenched with sat. NH₄Cl; ether is then added and the solution is brought to about pH 3 with 1 M HCl. The organic layer is separated, washed with sat. NaHCO₃ and sat. NaCl, and dried over Na₂SO₄. Removal of the solvent gives (Z)-3,7-dimethyl-2,7-octadien-1-ol.

E. The (Z)-3,7-dimethyl-2,7-octadien-1-ol is esterified by stirring, under nitrogen, 0.96 g (6.2 mmol) of the diene alcohol, 1.53 ml (12 mmol) of propionic anhydride and 1.5 ml of pyridine overnight. Ice is then added to the mixture, and after 30 min the reaction is poured into pentane/5% HCl. The organic fraction is separated and washed with 2 M Na₂CO₃ and sat. NaCl, and dried over Na₂SO₄. Removal of the solvent gives the crude product, which is then purified by plating on silica gel plates developing with ether/hexane to yield (Z)-3,7-dimethyl-2,7-octadien-1-yl propionate.

B.p. 60° (microdistillation bath) @0.25 mm.

EXAMPLE 5

A solution of 4.7 g (23.0 mmol) of cuprous bromide/dimethyl sulfide complex (prepared as in Example 1C), 20 ml of ether and 42 ml of dimethyl sulfide, under nitrogen, is cooled to about −50°. A 0.41 M solution of 4-methyl-4-penten-1-yl magnesium bromide (51 ml, 21.9 mmol) (prepared as in Example 1B) is added over a 1 hr period. The reaction is stirred approximately 1.5 hr, and then about 4 ml propyne is added and the mixture is warmed to −20°. After 1 hr, 25 ml of HMPA and triethylphosphite are added, followed by excess carbon dioxide. The mixture is warmed to −15° and placed in a CCl$_4$/CO$_2$ bath, and carbon dioxide is bubbled into the reaction overnight. The reaction is worked up by adding (NH$_4$)$_2$SO$_4$, then filtered. The remaining solid is extracted with ether 4X and filtered. The filtrate (organic and aqueous phases) is salted with NaCl and extracted 3X with ether. The combined ether layers are extracted 3X with NaOH, and the NaOH layers are washed with ether, then acidified with H$_2$SO$_4$. The aqueous layer is salted out (NaCl), extracted with ether, washed with brine and dried over NaSO$_4$ to yield (Z)-3,7-dimethyl-2,7-octadienoic acid.

To 2.0 g (12.0 mmol) of (Z)-3,7-dimethyl-2,7-octadienoic acid is added dropwise about 40 ml of diazomethane, and the solution is stirred overnight. The reaction is poured into water and extracted with ether. The ether fraction is washed with sat. NaCl and dried over Na$_2$SO$_4$. Removal of the solvent and plating of the crude product on silica gel plates developing with 4% ether/hexane give the methyl ester of (Z)-3,7-dimethyl-2,7-octadienoic acid.

Reduction of the above methyl ester to the corresponding alcohol and esterification of the alcohol with propionic anhydride follow (using the methods of Example 4), yielding the final product, (Z)-3,7-dimethyl-2,7-octadien-1-yl propionate.

What is claimed is:

1. A compound of the formula:

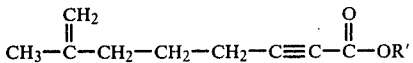

wherein R' is hydrogen or lower alkyl of one to five carbon atoms.

2. A compound according to claim 1 wherein R' is hydrogen.

3. A compound according to claim 1 wherein R' is methyl or ethyl.

4. A compound according to claim 3 wherein R' is methyl.